United States Patent
Nojiri et al.

(10) Patent No.: US 9,783,796 B2
(45) Date of Patent: Oct. 10, 2017

(54) AMIDASE, GENE FOR THE SAME, VECTOR, TRANSFORMANT, AND METHOD FOR PRODUCTION OF OPTICALLY ACTIVE CARBOXYLIC ACID AMIDE AND OPTICALLY ACTIVE CARBOXYLIC ACID BY USING ANY ONE OF THOSE ITEMS

(75) Inventors: Masutoshi Nojiri, Takasago (JP); Daisuke Moriyama, Takasago (JP); Tozo Nishiyama, Takasago (JP); Naoaki Taoka, Takasago (JP)

(73) Assignee: KANEKA CORPORATION, Osaka (JP)

( * ) Notice: Subject to any disclaimer, the term of this patent is extended or adjusted under 35 U.S.C. 154(b) by 2036 days.

(21) Appl. No.: 12/532,290

(22) PCT Filed: Mar. 14, 2008

(86) PCT No.: PCT/JP2008/054704
§ 371 (c)(1),
(2), (4) Date: Feb. 23, 2010

(87) PCT Pub. No.: WO2008/120554
PCT Pub. Date: Oct. 9, 2008

(65) Prior Publication Data
US 2013/0059348 A1    Mar. 7, 2013

(30) Foreign Application Priority Data
Mar. 22, 2007   (JP) ................................. 2007-074463

(51) Int. Cl.
| | | |
|---|---|---|
| C12N 1/20 | (2006.01) |
| C12N 15/00 | (2006.01) |
| C12N 9/86 | (2006.01) |
| C12P 13/02 | (2006.01) |
| C07H 21/04 | (2006.01) |
| C12N 9/80 | (2006.01) |
| C12P 41/00 | (2006.01) |

(52) U.S. Cl.
CPC ................ *C12N 9/80* (2013.01); *C12P 13/02* (2013.01); *C12P 41/006* (2013.01)

(58) Field of Classification Search
None
See application file for complete search history.

(56) References Cited

FOREIGN PATENT DOCUMENTS

JP    2004-105152    4/2004

OTHER PUBLICATIONS

UniProt Accession No. Q472C5 (Amidase, created Sep. 13, 2005).*
Egorova et al. Purification and properties of an enantioselective and thermoactive amidase from the thermophilic actinomycete Pseudonocardia thermophila, Appl Microbiol Biotechnol (2004), 65: 38-45.*
XP008112461 Hidenobu Komeda et al., "A novel R-stereoselective amidase from *Pseudomonas* sp. MCI3434 acting on piperazine-2-tert-butylcarboxamide", European Journal of Biochemistry, vol. 271, No. 8, Apr. 1, 2004, pp. 1580-1590.
XP002613798 Database UniProt [Online], Sep. 13, 2005, "SubName: Full=Amidase," XP002613798, retrieved from EBI accession No. UNIPROT:Q472O5.
Extended European Search Report dated Dec. 10, 2010 issued in counterpart Application No. EP08722100.
English translation of International Preliminary Report on Patentability (Chapter I), Dated Sep. 22, 2009, in International Application No. PCT/JP2008/054704.

* cited by examiner

*Primary Examiner* — Iqbal H Chowdhury
(74) *Attorney, Agent, or Firm* — Polsinelli PC

(57) ABSTRACT

The present invention has its object to provide a novel polypeptide having amidase activity to selectively hydrolyze S-enantiomer in racemic nipecotamide, a DNA encoding the polypeptide, a vector containing the DNA, a transformant transformed with the vector, and a method for producing an optically active carboxylic acid amide and an optically active carboxylic acid in which a racemic carboxylic acid amide is hydrolyzed with the polypeptide or the transformant.

10 Claims, No Drawings

US 9,783,796 B2

AMIDASE, GENE FOR THE SAME, VECTOR, TRANSFORMANT, AND METHOD FOR PRODUCTION OF OPTICALLY ACTIVE CARBOXYLIC ACID AMIDE AND OPTICALLY ACTIVE CARBOXYLIC ACID BY USING ANY ONE OF THOSE ITEMS

CROSS REFERENCE TO RELATED APPLICATIONS

This application is a National Phase filing under 35 U.S.C. §371 of PCT/JP2009/054704 filed Mar. 14, 2008, which claims priority to Patent Application No. 2007-074463, filed in Japan on Mar. 22, 2007. The entire contents of each of the above-applications are incorporated herein by reference.

TECHNICAL FIELD

The present invention relates to a novel polypeptide having activity to selectively hydrolyze S-enantiomer in racemic nipecotamide, a DNA encoding the polypeptide, a vector containing the DNA, a transformant transformed with the vector, and a method for producing an optically active carboxylic acid amide and an optically active carboxylic acid using any of these.

BACKGROUND ART

Optically active carboxylic acid amides and optically active carboxylic acids, in particular, optically active nipecotamide, and optically active nipecotic acid are useful as synthetic materials or synthetic intermediates of agricultural chemicals, medicaments and the like. As is known in the conventional art, racemic nipecotamide is hydrolyzed through action of an amidase derived from *Pseudomonas* sp. MCI3434 strain (Patent Document 1, Non-Patent Document 1). However, the stereoselectivity and productivity of the amidase are unknown.
Patent Document 1: JP-A 2004-105152
Non-Patent Document 1: Eur. J. Biochem., 2004, vol. 271, p. 1580

SUMMARY OF THE INVENTION

An object of the present invention is to provide a novel amidase having activity to stereoselectively hydrolyze racemic nipecotamide, a DNA encoding the amidase, a vector containing the DNA, a transformant transformed with the vector, and a method for producing an optically active carboxylic acid amide and an optically active carboxylic acid using any of these.

In view of the state of the art, the present inventors intensively studied, and finally isolated an amidase capable of selectively hydrolyzing S-enantiomer in racemic nipecotamide from *Cupriavidus* sp. KNK-J915 strain (FERM BP-10739), and obtained a DNA encoding the amidase. The present inventors also found out that a highly stereoselective hydrolysis reaction of carboxylic acid amides proceeds in high yield by a transformant that produces a large amount of the amidase, or a high-concentration solution of the amidase, which are obtainable by using the DNA. Thus, the present inventors completed the present invention.

The present invention has one or more of the following technical feature(s).

(1) One feature of the present invention is a polypeptide which is any one of the following polypeptides (a), (b), and (c):

(a) a polypeptide comprising the amino acid sequence shown under SEQ ID NO:1 in the sequence listing;

(b) a polypeptide comprising an amino acid sequence derived from the amino acid sequence shown under SEQ ID NO:1 in the sequence listing by substitution, insertion; deletion, and/or addition of one or plurality of amino acids, and having activity to selectively hydrolyze S-enantiomer in racemic nipecotamide; and (c) a polypeptide having sequence identity of 70% or higher to the amino acid sequence shown under SEQ ID NO:1 in the sequence listing, and having activity to selectively hydrolyze S-enantiomer in racemic nipecotamide.

(2) Another feature of the present invention is a polypeptide having the following physicochemical properties:

(a) activity to selectively hydrolyze S-enantiomer in racemic nipecotamide;

(b) a molecular weight of about 52 kDa as determined by SDS-PAGE;

(c) an optimum pH of from 8 to 9 for an amidase reaction using racemic nipecotamide as a substrate;

(d) an optimum temperature of 50° C. for the amidase reaction using racemic nipecotamide as the substrate; and (e) stability at a pH of around 7 and at a temperature of 50° C. or lower.

(3) Still another feature of the present invention is a DNA which is any one of the following DNAs (a), (b), and (c):

(a) a DNA comprising the base sequence shown under SEQ ID NO:2 in the sequence listing;

(b) a DNA hybridizable under a stringent condition with a DNA comprising a base sequence complementary to the base sequence shown under SEQ ID NO:2 in the sequence listing, and encoding a polypeptide having activity to selectively hydrolyze S-enantiomer in racemic nipecotamide; and (c) a DNA having sequence identity of 70% or higher to the base sequence shown under SEQ ID NO:2 in the sequence listing, and encoding a polypeptide having activity to selectively hydrolyze S-enantiomer in racemic nipecotamide.

(4) Still another feature of the present invention is a vector comprising the DNA.

(5) Still another feature of the present invention is a transformant which is producible by transformation of a host cell with the vector.

(6) Still another feature of the present invention is a method for producing an optically active carboxylic acid amide and an optically active carboxylic acid, which comprises: allowing the polypeptide or the transformant to act on a racemic carboxylic acid amide; and isolating an optically active carboxylic acid and an optically active carboxylic acid amide produced.

The present invention provides a novel amidase, a DNA encoding the amidase, a vector containing the DNA, a transformant transformed with the vector, and a method for producing an optically active carboxylic acid amide and an optically active carboxylic acid using any of these.

Hereinafter, the present invention will be described in detail by way of embodiments. The present invention is not intended to be limited to these.

Gene manipulations including isolation of a DNA, preparation of a vector and transformation in the present description may be conducted in accordance with a manner described in publications such as Molecular Cloning 2nd Edition (Cold Spring Harbor Laboratory Press, 1989) and Current Protocols in Molecular Biology (Greene Publishing Associates and Wiley-Interscience) unless otherwise indicated. The sign "%" used herein means "% (w/v)" unless otherwise specified.

1. Amidase and Polypeptide

The present invention relates to a novel amidase having the following physicochemical properties:

(a) activity to selectively hydrolyze S-enantiomer in racemic nipecotamide;

(b) a molecular weight of about 52 kDa as determined by SDS-PAGE;

(c) an optimum pH of from 8 to 9 for an amidase reaction using racemic nipecotamide as a substrate;

(d) an optimum temperature of 50° C. for the amidase reaction using racemic nipecotamide as the substrate; and (e) stability at a pH around 7 and at a temperature of 50° C. or lower.

The amidase of the present invention is a polypeptide having activity to selectively hydrolyze S-enantiomer in racemic nipecotamide, and activity to produce an optically active carboxylic acid amide and an optically active carboxylic acid. Such a polypeptide can be isolated from organisms such as microorganisms having the above-mentioned activity. Microorganisms used as a source of the polypeptide of the present invention are not particularly limited, but a candidate is a bacterium that belongs to the genus *Cupriavidus*. Especially, *Cupriavidus* sp. KNK-J915 strain (FERM BP-10739) is preferably used. The strain (KNK-J915) was isolated from soil by the present inventors.

*Cupriavidus* sp. KNK-J915 strain was deposited with International Patent Organism Depositary, National Institute of Advanced Industrial Science and Technology (Tsukuba Central 6, 1-1-1 Higashi, Tsukuba, Ibaraki, Japan) on Nov. 28, 2006, under the accession number FERM BP-10739. The bacteriological properties of *Cupriavidus* sp. KNK-J915 strain are listed below.

A. Form (1) Cell form: bacillary form with a size of 0.8 to 1.0×1.5 to 2.5 μm (2) Nonmotile (3) Asporogenous (4) Gram negative (5) Colony form: circular, convex, smooth marginal, and yellowish B. Physiological property (1) Gelatin hydrolysis: negative (2) Starch hydrolysis: negative (3) Nitrate reduction: positive (4) Catalase: positive (5) Oxidase: positive (6) Urease: negative (7) O-F test: negative (both for oxidation and fermentation)

(8) Carbohydrate decomposition: incapable of hydrolyzing Tween80; incapable of producing an acid from adonitol, salicin, inositol, mannitol, sorbitol, mannose, raffinose, saccharose, maltose, cellobiose, galactose, lactose, glycerol, D-ribose, and L-arabinose; and capable of oxidizing fructose.

The microorganisms that produce the polypeptide of the present invention are either of a wild type or a variant. Alternatively, a microorganism induced to produce the polypeptide by genetic techniques such as cell fusion or genetic manipulations may also be used. The genetically manipulated microorganism that produces the polypeptide of the present invention can be obtained by a method including the steps of: isolating and/or purifying the enzyme and determining a part of or the entire amino acid sequence of the enzyme; determining the nucleotide sequence encoding the polypeptide based on the amino acid sequence; obtaining nucleotides of the nucleotide sequence encoding the polypeptide based on the amino acid sequence; introducing the nucleotide sequence into another microorganism to obtain a recombinant microorganism; and culturing the recombinant microorganism to obtain the enzyme of the present invention.

One embodiment of the polypeptide of the present invention is a polypeptide having the amino acid sequence shown under SEQ ID NO:1 in the sequence listing. Polypeptides that have sequence identity of higher than a certain level to the polypeptide having the amino acid sequence shown under SEQ ID NO:1 in the sequence listing and have activity to selectively hydrolyze S-enantiomer in racemic nipecotamide are equivalent to the polypeptide of the present embodiment, and encompassed by the present invention.

Here, the sequence identity between two amino acid sequences is indicated by, for example, a score that indicates the identity to the full length of the sequence, and is determined by comparative analysis of the two amino acid sequences using the homology search program BLAST (W. R. Pearson & D. J. Lipman, P.N.A.S. (1988) 85: 2444-2448). Examples of the polypeptides having sequence identity of higher than a certain level to the polypeptide having the amino acid sequence shown under SEQ ID NO:1 in the sequence listing include polypeptides having sequence identity of 70% or higher to the polypeptide shown under SEQ ID NO:1. The sequence identity of the peptides is preferably 80% or higher, more preferably 85% or higher, still more preferably 90% or higher, and further more preferably 95% or higher.

Homology search of the amino acid sequence shown under SEQ ID NO:1 in the sequence listing using the homology search program BLAST revealed that the sequence identity to an amidase derived from *Ralstonia eutropha* JMP134 strain was about 78%, and the sequence identity to an amidase derived from *Ralstonia metallidurans* CH34 strain was about 73%. These amino acid sequences are registered in the database of National Center for Biotechnology Information (http://www.ncbi.nlm.nih.gov/) under the accession numbers of YP_295602 and YP_584021, respectively, and available to anyone.

The polypeptide of the present invention is obtained, for example, as follows: ligating a DNA to be hybridized with a DNA having the base sequence complementary to the base sequence shown under SEQ ID NO:2 in the sequence listing under a stringent condition with a suitable vector; introducing the vector into a suitable host cell; and allowing expression of the polypeptide.

The polypeptide of the present invention may have the amino acid sequence derived from the amino acid sequence shown under SEQ:ID 1 in the sequence listing by substitution, insertion, deletion, or addition of amino acids by known techniques described in publications such as Current Protocols in Molecular Biology (John Wiley and Sons, Inc., 1989). The number of amino acids to be substituted, inserted, deleted or added is not limited as long as the variant polypeptide still has activity that characterizes the polypeptide of the present embodiment. However, the number is preferably 90 or less, more preferably decreased to 65 or less, still more preferably 45 or less, and further more preferably 20 or less.

The microorganism as a source of the polypeptide of the present invention can be cultured in any common liquid nutrient medium containing nutrients such as carbon sources, nitrogen sources, inorganic salts, and organic nutrients as long as the microorganism can propagate therein.

The polypeptide of the present invention can be isolated from the microorganism of the source of the polypeptide by suitably using known protein purification techniques in combination. For example, the polypeptide of the present invention can be isolated as follows. First, the microorganism is cultured in a suitable medium. Then, cells are collected by centrifugation or filtration from the culture solution. The obtained cells are disrupted by physical procedure using an ultrasonic disintegrator, glass beads or the like. Subsequently, cell residues are removed by centrifugation to obtain a cell-free extract, and the polypeptide of the present invention is isolated from the cell-free extract using any of the following techniques alone or in combination: salting out (ammonium sulfate precipitation, sodium phosphate precipitation, etc.), solvent precipitation (protein fraction precipitation using acetone, ethanol, etc.), dialysis, gel filtration chromatography, ion exchange chromatography, reversed phase chromatography, and ultra filtration.

The physical and enzymological properties of the polypeptide that is isolated from *Cupriavidus* sp. KNK-J915 strain (FERM BP-10739) and has the amino acid sequence shown under SEQ ID NO:1 are listed below.

1. Molecular weight: 52000 (determined by SDS-PAGE), 200000 (determined by gel filtration)
2. Subunit: tetramer
3. Optimum pH for amidase reaction: pH 8.0 to 9.0
4. Optimum temperature for amidase reaction: 50° C.
5. Thermal stability: stable at 50° C. or lower
6. Substrate specificity: especially strong activity on heterocyclic compounds such as nipecotamide, N-benzylnipecotamide, pipecolic acid amide, isonipecotamide and indoline carboxylic acid amide, and aliphatic amides such as propionic acid amide, isobutylamide, mandelic acid amide and phenylpropionic acid amide. Examples of more preferable substrates include (S)-nipecotamide, (R)-pipecolic acid amide, (R)-indoline carboxylic acid amide and (S)-phenylpropionic acid amide.

2. DNA

The DNA of the present invention encodes the polypeptide having activity to selectively hydrolyze S-enantiomer in racemic nipecotamide, and activity to produce an optically active carboxylic acid amide and an optically active carboxylic acid. The base sequence of the DNA is not limited as long as the DNA is introduced into a host cell by the procedure described below and expresses the polypeptide in the host cell. The DNA may include non-coding regions. A person skilled in the art who obtains the polypeptide of the present invention could acquire the DNA of the present invention from a microorganism of a source of the polypeptide of the present invention by a known procedure. For example, the DNA of the present invention can be obtained as follows.

First, the polypeptide of the present invention that has been isolated is digested with suitable endopeptidases. The obtained peptide fragments are separated by reversed phase HPLC. Then, apart of or the entire amino acid sequence of the peptide fragments is determined using a protein sequencer such as ABI 492 protein sequencer (product of Applied Biosystems).

A PCR (Polymerase Chain Reaction) primer for amplifying apart of the DNA encoding the polypeptide is synthesized based on the amino acid sequence information thus obtained. Next, a chromosomal DNA of the microorganism used as the source of the polypeptide is prepared by a common DNA isolation technique such as the technique described in Visser et al. (Appl. Microbiol. Biotechnol., 53, 415 (2000)). Apart of DNA encoding the polypeptide is amplified by PCR using the PCR primer and the chromosomal DNA as a template, and the base sequence thereof is determined. The base sequence may be determined using a DNA sequencer such as ABI 3130xl DNA sequencer (product of Applied Biosystems).

Using the obtained partial base sequence of the DNA encoding the polypeptide, the entire base sequence of the DNA encoding the polypeptide can be determined by, for example, i-PCR (Nucl. Acids Res., 16, 8186 (1988)).

One embodiment of the DNA of the present invention obtained as described above is a DNA containing the base sequence shown under SEQ ID NO:2 in the sequence listing. A DNA comprising a base sequence derived from the base sequence shown under SEQ ID NO:2 in the sequence listing by substitution, insertion, deletion, and/or addition of one or plurality of bases, and encoding a polypeptide having activity to selectively hydrolyze S-enantiomer in racemic nipecotamide is encompassed by the present invention. The number of the bases indicated by the term "plurality of bases" is not limited as long as the polypeptide encoded by the DNA has the above-mentioned activity. However, the number is preferably 270 or less, more preferably 200 or less, still more preferably 130 or less, and further more preferably 70 or less.

A DNA that encodes the polypeptide having the above-mentioned activity and has sequence identity of 70% or more to the base sequence shown under SEQ ID NO:2 in the sequence listing is encompassed by the present invention. The sequence identity is preferably 80% or more, more preferably 85% or more, still more preferably 90% or more, and further more preferably 95% or more.

A DNA that is hybridizable under a stringent condition with a DNA containing the base sequence complementary to the base sequence shown under SEQ ID NO:2 in the sequence listing, and that encodes a polypeptide having activity to selectively hydrolyze S-enantiomer in racemic nipecotamide is also encompassed by the present invention. In addition, a DNA that is hybridizable under a stringent condition with a DNA containing the base sequence complementary to the base sequence shown under SEQ ID NO:2 in the sequence listing, and that encodes a polypeptide having activity to hydrolyze a racemic carboxylic acid amide to produce an optically active carboxylic acid amide and an optically active carboxylic acid is also encompassed by the present invention.

Here, "the DNA hybridizable under a stringent condition with a DNA having the base sequence complementary to the base sequence shown under SEQ ID NO:2 in the sequence listing" means a DNA obtainable by a hybridization technique such as colony hybridization, plaque hybridization or Southern hybridization under a stringent condition using a DNA having the base sequence complementary to the base sequence shown under SEQ ID NO:2 in the sequence listing as a probe.

The hybridization may be carried out, for example, in accordance with a manner described in literatures such as Molecular Cloning 2nd Edition (Cold Spring Harbor Laboratory Press, 1989). Here, examples of the "DNA hybridizable under a stringent condition" include DNAs, which are obtainable through hybridization with a filter, onto which a colony- or plaque-derived DNA is immobilized, in the presence of 0.7 to 1.0 M NaCl, at 65° C., followed by washing the filter with a 2-fold concentration of SSC solution (one-fold concentration of the SSC solution consists of 150 mM NaCl and 15 mM sodium citrate) at 65° C. Preferable examples of the DNA include DNAs obtainable by washing the filter with half-fold concentration of the SSC solution at 65° C. More preferable examples thereof include DNAs obtainable by washing the filter with 0.2-fold concentration of the SSC solution at 65° C. Still more preferable examples thereof include DNAs obtainable by washing with 0.1-fold concentration of the SSC solution at 65° C.

Gene manipulations described in the present description including isolation of the DNA, and preparation of a vector and transformation described below may be conducted in accordance with a manner described in publications such as Molecular Cloning 2nd Edition (Cold Spring Harbor Laboratory Press, 1989) unless otherwise indicated.

3. Vector

The vector of the present invention is not particularly limited as long as the gene encoded in the DNA can be expressed in a suitable host cell. Examples of the vector include plasmid vectors, phage vectors and cosmid vectors. Shuttle vectors that can transfer DNA between host cells of different species can also be used.

Such a vector normally contains regulatory sequences such as lacUV5 promoter, trp promoter, trc promoter, tac promoter, lpp promoter, tufB promoter, recA promoter and pL promoter, and is suited for use as an expression vector containing an expression unit ligated to the DNA of the present invention while maintaining functions thereof. For example, a plasmid pUCN18 is suitably used. The plasmid pUCN18 has the same base sequence as that of the plasmid pUC18 (product of Takara Bio, Inc., GenBank Accession No. L09136), but its NdeI site is destroyed by a T to A substitution at nucleotide position 185, and a new NdeI site is introduced by a GC to TG substitution at nucleotide positions 471 and 472 by PCR.

Examples of the above-mentioned regulatory sequences include base sequences having a functional promoter sequence and base sequences having any related transcription regulatory sequences (e.g. enhancer, CCAAT box, TATA box, SPI site, etc.).

The term "ligated to the DNA of the present invention while maintaining functions thereof" means that a gene, and various regulatory elements such as a promoter and an enhancer, which regulate expression of the gene, are linked together so that each element can function in a host cell. It would be well known to a person skilled in the art that the type and function of the regulatory factor may vary depending on the host. Examples of the vector of the present invention include the later described plasmid pNCS, which is obtainable by introducing the DNA shown under SEQ ID NO:2 into the plasmid pUCN18 (see Example 4)

4. Host Cell

Examples of the host cell used herein include bacteria, yeast, filamentous fungi, plant cells and animal cells. However, for introduction efficiency and expression efficiency, bacteria are preferable, and *Escherichia coli* is particularly preferable. A vector containing the DNA of the present invention can be introduced into a host cell by processes known in the art. When the host cell is an *Escherichia coli* cell, the vector can be introduced into the host cell using a commercially available *Escherichia coli* HB101 competent cell (product of Takara Bio, Inc.).

5. Transformant

"The transformant of the present invention" is obtainable by inserting the DNA encoding the polypeptide of the present invention into the vector, and then introducing the vector into the host cell. It should be noted that "the transformant of the present invention" includes cultured cells as well as processed products of the cultured cells. The processed products used herein mean cells processed with a surfactant or an organic solvent, dried cells, disrupted cells, crude extract of the cells, and materials on which the above-mentioned cells or extraction are immobilized by a method known in the art. These processed products are usable in the reaction in the present invention as long as these still have activity to selectively hydrolyze S-enantiomer in racemic nipecotamide. The transformant of the present invention can be cultured in any common liquid nutrient medium containing nutrients such as carbon sources, nitrogen sources, inorganic salts, and organic nutrients as long as it can propagate therein.

Examples of the transformant include *E. coli* HB101 (pNCS) described later in Examples.

6. Method for Producing Optically Active Carboxylic Acid Amide and Optically Active Carboxylic Acid "The method for producing an optically active carboxylic acid amide and an optically active carboxylic acid" of the present invention includes a step of adding a racemic carboxylic acid amide serving as a substrate, and the polypeptide of the present invention or the transformant containing the DNA encoding the polypeptide, in a suitable solvent.

For the reaction, an aqueous medium or a mixture of an aqueous medium and organic solvent may be used. Examples of the organic solvent include toluene, ethyl acetate, n-butyl acetate, hexane, isopropanol, diisopropyl ether, methanol, acetone and dimethyl sulfoxide. The reaction is conducted, for example, at a temperature of 10° C. to 70° C. with the pH of the reaction liquid kept in the range of 4 to 10. The reaction may be carried out by batch reaction or sequential reaction. For batch reaction, for example, a reaction substrate may be added at a concentration of 0.1 to 70% (w/v) in total volume of the loaded reaction mixture.

Examples of "the racemic carboxylic acid amide" serving as a substrate include racemic nipecotamide, racemic pipecolic acid amide, racemic indoline carboxylic acid amide and racemic phenyl propionic acid amide. However, "the racemic carboxylic acid amide" serving as a substrate is not limited to these compounds as long as it is hydrolyzed under the above-mentioned reaction conditions so as to be converted to an optically active amide and an optically active carboxylic acid. Use of racemic nipecotamide as the substrate under the above-mentioned reaction conditions yields (R)-nipecotamide and (S)-nipecotic acid; use of racemic pipecolic acid amide as the substrate yields (S)-pipecolic acid amide and (R)-pipecolic acid; use of racemic indoline carboxylic acid amide as the substrate yields (R)-indoline carboxylic acid amide and (S)-indoline carboxylic acid; and use of racemic phenyl propionic acid amide as the substrate yields (R)-phenyl propionic acid amide and (S)-phenyl propionic acid. The amide and acid produced in the reaction (e.g. (R)-nipecotamide and (S)-nipecotic acid) can be separately isolated and purified by a common procedure. Namely, a reaction liquid containing (R)-nipecotamide produced in the hydrolysis reaction is extracted using an organic solvent such as ethyl acetate and toluene, and the organic solvent is removed under reduced pressure. Subsequently, a process such as distillation, recrystallization or chromatography is conducted to isolate and purify the amide and the acid. Alternatively, the reaction liquid is filtrated to remove the microorganism cells, and neutralization crystallization is carried out on the obtained filtrate using hydrochloric acid and the like. Then, precipitates of the target substance may be isolated and purified by filtration. The amide and acid may also be isolated and purified by filtering the reaction liquid to remove the microorganism cells, adding di-t-butyldicarbonate and the like to the obtained filtrate to convert the products into derivatives and separating precipitates of the target substance by filtration.

EXAMPLES

The following examples illustrate the present invention in detail. However, the present invention is not limited to these examples.

(Example 1) Purification of Amidase Derived from *Cupriavidus* sp. KNK-J915 (FERM BP-10739)

In the following examples, the amidase activity was determined by the following procedure. To 100 mM phosphate buffer (pH 7.0) were added 1% N-benzylnipecotamide and an enzyme solution, and allowed to react for 1 hour at 30° C. Then, the solution was analyzed under high speed liquid chromatography analysis conditions A. Enzyme activity which produces 1 µmol of N-benzylnipecotic acid per 1 minute under these conditions was defined as 1 unit.

High Speed Liquid Chromatography Analysis Condition A
Column: YMC-A303 (4.6 mmφ×250 mm, product of YMC Co., Ltd.)
Eluant: 20 mM phosphate aqueous solution (pH 2.5)/acetonitrile=9/1
Flow rate: 1.0 ml/min
Column temperature: 30° C.
Measurement wavelength: 210 nm An amount of 100 ml of a liquid medium (pH 7.0) (composition: 1.0% meat extract; 1.5% polypeptone; 0.5% bacto yeast extract; and 0.3% NaCl) was poured into a 500-ml Sakaguchi flask, and steam-sterilized for 20 minutes at 120° C. The liquid medium was aseptically inoculated with *Cupriavidus* sp. KNK-J915 strain, and the strain was cultured with shaking at 35° C. for 72 hours to yield a culture solution in an amount of 4.2 L. The obtained culture solution was centrifuged to collect cells, and then the cells were washed with 500 ml of 100 mM phosphate buffer (pH 7.0), and suspended in 200 ml of 100 mM phosphate buffer (pH 7.0). The cells in the suspension were ultrasonically disrupted by an ultrasonic disintegrator (SONIFIER 250, product of BRANSON), and centrifuged to remove cell residues. Thus, a cell-free extract was obtained.

Ammonium sulfate was added to the cell-free extract to reach a saturation concentration of 20%. After being stirred for 30 minutes at 4° C., the mixture was centrifuged to remove formed precipitates. Additionally, ammonium sulfate was added to the supernatant to reach a saturation concentration of 40%. After being stirred for 30 minutes at 4° C., the mixture was centrifuged to obtain formed precipitates, and the precipitates were suspended in 100 mM phosphate buffer (pH 7.0), and dialyzed with 100 mM phosphate buffer (pH 7.0).

The dialyzed enzyme liquid was supplied to a 400-ml column (DEAE-TOYOPEARL 650M, product of Tosoh Corporation) that had been equilibrated in advance with 10 mM phosphate buffer (pH 8.0), and the enzyme was allowed to adsorb on the column. The column was washed with the same buffer, and an active fraction was eluted with a linear gradient of sodium chloride from 0 M to 0.3 M.

Ammonium sulfate was added to the active fraction to give a final concentration of 0.8 M. The obtained solution was supplied to a 75-ml column (Phenyl-TOYOPEARL 650M, product of Tosoh Corporation) that had been equilibrated with 10 mM phosphate buffer (pH 7.0) containing 0.8 M ammonium sulfate, and the enzyme was allowed to adsorb thereon. The column was washed with the same buffer, and an active fraction was eluted with a linear gradient of ammonium sulfate from 0.8 M to 0 M.

Ammonium sulfate was added to the active fraction to give a final concentration of 0.8 M. The obtained solution was supplied to a 25-ml column (Butyl-TOYOPEARL 650S, product of Tosoh Corporation) that had been equilibrated with 10 mM phosphate buffer (pH 7.0) containing 0.8 M ammonium sulfate, and the enzyme was allowed to adsorb thereon. The column was washed with the same buffer, and an active fraction was eluted with a linear gradient of ammonium sulfate from 0.8 M to 0 M.

After dialysis with 10 mM phosphate buffer (pH 8.0), the active fraction was supplied to a 6-ml column (Resource Q, product of Pharmacia Biotech) that had been equilibrated with 10 mM phosphate buffer (pH 8.0), and the enzyme was allowed to adsorb thereon. The column was washed with the same buffer solution, and an active fraction was eluted with a linear gradient of sodium chloride from 0 M to 0.5 M.

The enzyme contained in this active fraction was determined as a purified enzyme because the result of dodecyl-sodium-sulfate-polyacrylamide electrophoresis analysis of the active fraction showed a single band.

The specific activity of the purified enzyme was 1.7 U/mg-protein. Hereinafter, this enzyme is referred to as HCS.

(Example 2) Enzymological Property of Purified HCS

The Optimum pH and optimum temperature of an amidase reaction of the purified enzyme obtained in Example 1, and thermal stability of the enzyme were determined by quantifying N-benzylnipecotic acid produced in the hydrolysis reaction using N-benzylnipecotamide as a substrate, by HPLC. For determination of the optimum pH, the reaction was allowed to proceed at each pH for 1 hour at 30° C., and stopped by addition of acetonitrile. The resultant solution was analyzed under the high speed liquid chromatography analysis conditions A described in Example 1. For determination of the optimum temperature, the reaction was allowed to proceed at each temperature for 1 hour, and stopped by addition of acetonitrile. The resultant solution was analyzed under the high speed liquid chromatography analysis conditions A described in Example 1. For determining the thermal stability, after incubation at each temperature for 30 minutes, the reaction was allowed to proceed for 1 hour, and stopped by addition of acetonitrile. The resultant solution was analyzed under the high speed liquid chromatography analysis conditions A described in Example 1.

Table 1 shows the results.

TABLE 1

| | |
|---|---|
| Optimum reaction pH | pH 8.0 to 9.0 |
| Optimum reaction temperature | 50° C. |
| Thermal stability | Remaining activity 100% at 50° C. or below |

Next, the substrate specificity of HCS was analyzed. The substrate compound was added in a form of a 1% solution. The enzyme reaction was allowed to proceed at 30° C. in 100 mM phosphate buffer (pH 7.0). The resultant solution was analyzed under the high speed liquid chromatography analysis conditions A described in Example 1 or the high speed liquid chromatography analysis conditions B shown below.

High Speed Liquid Chromatography Analysis Condition B
Column: SUMICHIRAL OA-5000 (4.6 mmϕ×150 mm, product of Sumika Chemical Analysis Service, Ltd.)
Eluant: 2 mM $CuSO_4$ aqueous solution
Flow rate: 1.0 ml/min
Column temperature: 30° C.
Measurement wavelength: 254 nm Table 2 shows the activities relative to the activity on (R,S)-nipecotamide set to 100.

TABLE 2

| Substrate | Relative activity (%) |
|---|---|
| (R,S)-nipecotamide | 100 |
| (R,S)-N-benzylnipecotamide | 49 |
| (R,S)-pipecolic acid amide | 34 |
| isonipecotamide | 21 |
| indoline carboxylic acid amide | 64 |
| D,L-phenylalanine amide | 3.4 |
| D,L-β-phenylalanine amide | 0 |
| D,L-proline amide | 0 |
| D,L-alanine amide | 0 |
| D,L-leucine amide | 0 |
| benzamide | 5.4 |
| propionic acid amide | 59 |
| isobutylamide | 230 |
| (R,S)-mandelic acid amide | 49 |
| (R,S)-phenyl propionic acid amide | 309 |

HCS showed particularly strong amidase activity on heterocyclic compounds such as nipecotamide, N-benzylnipecotamide, pipecolic acid amide, isonipecotamide and indoline carboxylic acid amide, and aliphatic amides such as propionic acid amide, isobutylamide, mandelic acid amide and phenyl propionic acid amide, and weak amidase activity on phenylalanine amide and benzamide.

(Example 3) Cloning of HCS

The N-terminal-amino-acid sequence of the purified HCS obtained in Example 1 was analyzed using a protein sequencer (ABI 492, produced by Applied Biosystems). The purified HCS was denatured in the presence of 8 M urea, and digested with lysyl endopeptidase derived from an achromobacter species (product of Wako Pure Chemical Industries, Ltd.). The amino acid sequence of the obtained peptide fragments was determined. In consideration of the DNA sequence deduced from the amino acid sequence, primer 1 (SEQ ID NO:3 in the sequence listing) and primer 2 (SEQ ID NO:4 in the sequence listing) were synthesized. An amount of 50 µl of a buffer for ExTaq was prepared. This buffer contained the two primers (primer 1 and primer 2, each 40 pmol), chromosomal DNA derived from *Cupriavidus* sp. KNK-J915 strain (100 ng), dNTP (each 10 nmol) and ExTaq (2.5 U, product of TAKARA SHUZO Co., Ltd.). Heat denaturation (95° C., 1 minute), annealing (50° C., 1 minute), and an extension reaction (72° C., 0.5 minutes) were repeated for 30 cycles. The reaction fluid was cooled to 4° C., and then subjected to agarose gel electrophoresis to confirm amplification of the DNA. The chromosomal DNA of *Cupriavidus* sp. KNK-J915 strain used in the reaction was prepared in accordance with the small-scale preparation of bacterial genomic DNA taught in "Bunshiseibutugaku Jikkenn Protocol 1 (Current Protocols in Molecular Biology)" (Maruzen) p. 36.

The amplified DNA was subcloned into pT7Blue Vector (product of Novagen), and the base sequence thereof was determined. The result revealed that the amplified DNA has 196 bases except for the primer sequence. This sequence is hereinafter referred to as a "core sequence".

Based on a part close to the 5' end of the core sequence, primer 3 (SEQ ID NO:5 in the sequence listing) having a base sequence complementary to the base sequence of the part close to the 5' end of the core sequence was prepared, and primer 4 (SEQ ID NO:6 in the sequence listing) was prepared based on the base sequence of a part close to the 3' end of the core sequence. The chromosomal DNA of *Cupriavidus* sp. KNK-J915 strain was digested with restriction enzyme PstI, and the digested fragment was self-closed with T4 DNA ligase to obtain a circular DNA used as a template for inverse PCR. An amount of 50 µl of a buffer for ExTaq was prepared. This buffer contained the self-closed circular DNA (200 ng), the two primers (primer 3 and primer 4, each 50 pmol), dNTP (each 10 nmol) and ExTaq (2.5 U, product of TAKARA SHUZO Co., Ltd.). Heat denaturation (97° C., 1 minute), annealing (60° C., 1 minute), and an extension reaction (72° C., 5 minutes) were repeated for 30 cycles. The reaction fluid was cooled to 4° C., and then subjected to agarose gel electrophoresis to confirm amplification of the DNA.

The amplified DNA was subcloned into pT7Blue Vector (product of Novagen), and the base sequence thereof was determined. Based on the base sequence determined above and the core sequence, the entire base sequence of the gene encoding HCS derived from *Cupriavidus* sp. KNK-J915 strain was determined. The entire base sequence of the gene encoding HCS is shown as SEQ ID NO:2, and the deduced amino acid sequence encoded by the gene is shown as SEQ ID NO:1.

(Example 4) Construction of Recombinant Vector Containing HCS Gene

In order to obtain an *Escherichia coli* cell capable of expressing HCS, a recombinant vector used for transformation was constructed. First, a double strand DNA containing an NdeI site added to the initiation codon site of the HCS gene, and a new termination codon and an EcoRI site inserted immediately downstream of the original termination codon was prepared as follows.

Based on the base sequence determined in Example 3, primer 5 having the NdeI site added to the initiation codon site of the HCS gene (SEQ ID NO:7 in the sequence listing), and primer 6 having the EcoRI site inserted immediately downstream of the termination codon of the HCS gene (SEQ ID NO:8 in the sequence listing) were synthesized. An amount of 50 µl of a buffer for ExTaq was prepared. This buffer contained the two primers (primer 5 and primer 6, each 50 pmol), chromosomal DNA derived from *Cupriavidus* sp. KNK-J915 strain (10 ng), dNTP (each 10 nmol) and ExTaq (2.5 U, product of TAKARA SHUZO Co., Ltd.). Heat denaturation (97° C., 1 minute), annealing (60° C., 1 minute), and an extension reaction (72° C., 1.5 minutes) were repeated for 30 cycles. The reaction fluid was cooled to 4° C., and then subjected to agarose gel electrophoresis to confirm amplification of the DNA. The DNA fragment obtained by the PCR was digested with NdeI and EcoRI, and inserted between the NdeI recognition site and the EcoRI recognition site downstream of the lac promoter of the plasmid pUCN18 to construct recombinant vector pNCS. Here, the plasmid pUCN18 is a plasmid having a base sequence in which the NdeI site is destroyed by a T to A substitution at nucleotide position 185 of pUC18 (product of Takara Bio, Inc., GenBank Accession No. L09136), and a new NdeI site is introduced by a GC to TG substitution at nucleotide positions 471 and 472, by PCR.

(Example 5) Preparation of Transformant

The recombinant vector pNCS constructed in Example 4 was transformed into competent cells of E. coli HB 101 (product of Takara Bio, Inc.) to obtain E. coli HB101 (pNCS).

The bacteriological properties of E. coli HB101 are shown in various publications including "BIOCHEMICALS FOR LIFE SCIENCE" (Toyobo Co., Ltd., 1993, p. 116-119), and are known to those skilled in art. E. coli HB101 (pNCS) has acquired activity to produce the specific enzyme by gene recombination in addition to the same bacteriological properties as those of E. coli HB101.

(Example 6) Expression of HCS in Transformant

The transformant obtained in Example 5, and the transformant E. coli HB101 (pUCN18) containing vector plasmid pUCN18 (Comparative Example) were separately inoculated into 5 ml of a 2xYT culture medium (triptone 1.6%, yeast extract 1.0% and NaCl 0.5%; pH 7.0) containing 200 µg/ml of ampicillin, and cultured with shaking for 24 hours at 37° C. Cells were collected by centrifugation, and suspended in 5 ml of 100 mM phosphate buffer (pH 7.0). The cells were disrupted using an ultrasonic homogenizer (UH-50, product of SMT Co., Ltd), and cell residues were removed by centrifugation to obtain a cell-free extract. Table 3 shows the specific activity determined based on the measured amidase activity of the cell-free extracts.

TABLE 3

|  | Specific activity of cell-free extract (U/mg-protein) |
|---|---|
| E. coli HB101 (pUCN18) | 0 |
| E. coli HB101 (pNCS) | 1.2 |

As shown in Table 3, expression of amidase activity was found in the transformant obtained in Example 5. The amidase activity was measured by the procedure described in Example 1.

(Example 7) Selective Hydrolysis of S-Enantiomer in Racemic Nipecotamide

An amount of 10.1 g of racemic nipecotamide was dissolved in water to prepare a substrate solution having a pH adjusted to 8.0. To 200 ml of the prepared substrate solution was added 2 ml of a culture solution obtained by culturing E. coli HB101 (pNCS) as in Example 6, and stirred for 25 hours at 45° C. After completion of the reaction, the reaction liquid was heated for 30 minutes at 70° C., and centrifuged to remove solid matters including cells. Subsequently, the substrate and the product in the reaction liquid were converted into derivatives with benzyl chloroformate. The obtained derivatives were analyzed by high speed liquid chromatography to determine the conversion ratio (%) and optical purity (% e.e.). The results showed that the conversion rate was 50.2%, the optical purity of (R)-nipecotamide was 98.3% e.e., and the optical purity of (S)-nipecotic acid was 97.1% e.e.

Conversion ratio (%)=$P/(S_1+P) \times 100$ (P: amount of product (mol), $S_1$: amount of residual substrate (mol))

Optical purity (% e.e.)=$(A-B)/(A+B) \times 100$ (A represents the amount of the target enantiomer, and B represents the amount of the corresponding enantiomer.)
High Speed Liquid Chromatography Analysis Condition
[Analysis of Conversion Ratio]
 Column: YMC-A303 (4.6 mmφ×250 mm, product of YMC Co., Ltd.)
 Eluant: 20 mM phosphate aqueous solution (pH 2.5)/acetonitrile=7/3
 Flow rate: 1.0 ml/min
 Column temperature: 35° C.
 Measurement wavelength: 210 nm
[Optical Purity Analysis]
 Column: CHIRALPAK AD-RH (4.6 mmφ×150 mm, product of DAICEL CHEMICAL INDUSTRIES, LTD.)
 Eluant: 20 mM phosphate aqueous solution (pH 2.5)/acetonitrile=7/3
 Flow rate: 0.5 ml/min
 Column temperature: room temperature
 Measurement wavelength: 210 nm (Example 8) Selective Hydrolysis of R-Enantiomer in Racemic Pipecolic Acid Amide To 100 mM phosphate buffer (pH 7.0) were added 1% racemic pipecolic acid amide and the purified enzyme solution obtained in Example 1, and allowed to react at 30° C. Then high speed liquid chromatography analysis was conducted to determine the conversion ratio (%) and optical purity (% e.e.). The results showed that the conversion ratio was 18.3%, and the optical purity of (R)-pipecolic acid was 80.1% e.e.

Conversion ratio (%)=$P/(S_1+P) \times 100$ (P: amount of product (mol), $S_1$: amount of residual substrate (mol))

Optical purity (% e.e.)=$(A-B)/(A+B) \times 100$ (A represents the amount of the target enantiomer, and B represents the amount of the corresponding enantiomer.)
High Speed Liquid Chromatography Analysis Condition
[Analysis of Conversion Ratio and Optical Purity]
 Column: SUMICHIRAL OA-5000 (4.6 mmφ×150 mm, product of Sumika Chemical Analysis Service, Ltd.)
 Eluant: 2 mM $CuSO_4$ aqueous solution
 Flow rate: 1.0 ml/min
 Column temperature: 30° C.
 Measurement wavelength: 254 nm (Example 9) Selective Hydrolysis of R-Enantiomer in Racemic Indoline Carboxylic Acid Amide To 100 mM phosphate buffer solution (pH 7.0) were added 1% racemic indoline carboxylic acid amide and the purified enzyme solution obtained in Example 1. The obtained mixture was allowed to react at 30° C., and then the substrate and product in the reaction liquid were converted into derivatives with acetic anhydride. The conversion ratio (%) and optical purity (% e.e.) were determined by high speed liquid chromatography analysis of the obtained derivatives. The results showed that the conversion ratio was 39.2%, and the optical purity of (R)-indoline carboxylic acid was 97.8% e.e.

High Speed Liquid Chromatography Analysis Condition
[Analysis of Conversion Ratio]
Column: YMC-A303 (4.6 mmϕ×250 mm, product of YMC Co., Ltd.)
Eluant: 20 mM phosphate aqueous solution (pH 2.5)/acetonitrile=9/1
Flow rate: 1.0 ml/min
Column temperature: 30° C.
Measurement wavelength: 210 nm
[Analysis of Optical Purity]
Column: SUMICHIRAL OA-5000 (4.6 mmϕ×150 mm, product of Sumika Chemical Analysis Service, Ltd.)
Eluant: 2 mM $CuSO_4$ aqueous solution/methanol=7/3
Flow rate: 2.0 ml/min
Column temperature: 35° C.
Measurement wavelength: 254 nm (Example 10) Selective Hydrolysis of S-Enantiomer of Racemic Phenyl Propionic Acid Amide To 100 mM phosphate buffer (pH 7.0) were added 1% racemic phenyl propionic acid amide and the purified enzyme solution obtained in Example 1, and allowed to react at 30° C. The conversion ratio (%) and optical purity (% e.e.) were determined by high speed liquid chromatography analysis. The results showed that the conversion ratio was 36.0%, and the optical purity of (S)-phenyl propionic acid was 89.1% e.e.
High Speed Liquid Chromatography Analysis Condition
[Analysis of Conversion Ratio]
Column: YMC-A303 (4.6 mmϕ×250 mm, product of YMC Co., Ltd.)
Eluant: 20 mM phosphate aqueous solution (pH 2.5)/acetonitrile=7/3
Flow rate: 1.0 ml/min
Column temperature: 35° C.
Measurement wavelength: 210 nm
[Analysis of Optical Purity]
Column: CHIRALPAK AD-H (4.6 mmϕ×250 mm, product of DAICEL CHEMICAL INDUSTRIES, LTD.)
Eluant: Hexane/isopropanol/TFA=95/5/0.02
Flow rate: 1.0 ml/min
Column temperature: 30° C.
Measurement wavelength: 254 nm (Example 11) Preparation of *Escherichia coli* Transformed with DNA Encoding Putative Amidase Derived from *Ralstonia eutropha* JMP134 Strain Primer 7 (SEQ ID NO:10 in the sequence listing) having the NdeI site added to the initiation codon site, and primer 8 (SEQ ID NO:11 in the sequence listing) having an SacI site immediately downstream of the termination codon were synthesized based on the base sequence (SEQ ID NO:9 in the sequence listing) encoding the putative amidase derived from *Ralstonia eutropha* JMP134 strain, which has high sequence identity to the base sequence of the present invention derived from *Cupriavidus* sp. KNK-J915 (FERM BP-10739) determined in Example 3. An amount of 50 μl of a buffer for ExTaq was prepared. This buffer contained the two primers (primer 7 and primer 8, each 50 pmol), chromosomal DNA derived from *Ralstonia eutropha* JMP134 strain (10 ng), dNTP (each 10 nmol) and ExTaq (2.5 U, product of TAKARA SHUZO Co., Ltd.). Heat denaturation (97° C., 1 minute), annealing (60° C., 1 minute), and an extension reaction (72° C., 1.5 minutes) were repeated for 30 cycles. The reaction fluid was cooled to 4° C. and subjected to agarose gel electrophoresis to confirm amplification of the DNA. The DNA fragment obtained by the PCR was digested with NdeI and SacI, and inserted between the NdeI recognition site and the SacI recognition site downstream of the lac promoter of the plasmid pUCN18 to construct a recombinant vector pNRE. The recombinant vector pNRE thus constructed was transformed into competent cells of *E. coli* HB 101 (product of Takara. Bio, Inc.) to obtain *E. coli* HB101 (pNRE).

(Example 12) Selective Hydrolysis of S-Enantiomer in Racemic N-Benzylnipecotamide Using *Escherichia coli* Transformed with DNA Encoding Putative Amidase Derived from *Ralstonia eutropha* JMP134 Strain To 100 mM phosphate buffer (pH 7.0) were added 1% racemic N-benzylnipecotamide and the culture solution of *E. coli* HB101 (pNRE) obtained in Example 11, and allowed to react at 30° C. Thereafter, the conversion ratio (%) and optical purity (% e.e.) were determined by high speed liquid chromatography analysis. The results showed that the conversion ratio was 50.1%, and the optical purity of residual (R)—N-benzylnipecotamide was 99.4% e.e.

Conversion ratio (%)=$P/(S_1+P)\times100$ (P: amount of product (mol), $S_1$: amount of residual substrate (mol))

Optical purity (% e.e.)=$(A-B)/(A+B)\times100$ (A represents the amount of the target enantiomer, and B represents the amount of the corresponding enantiomer.)
High Speed Liquid Chromatography Analysis Condition
[Analysis of Conversion Rate]
Column: YMC-A303 (4.6 mmϕ×250 mm, product of YMC Co., Ltd.)
Eluant: 20 mM phosphate aqueous solution (pH 2.5)/acetonitrile=9/1
Flow rate: 1.0 ml/min
Column temperature: 35° C.
Measurement wavelength: 210 nm
[Analysis of Optical Purity]
Column: CHIRALPAK AD-RH (4.6 mmϕ×150 mm, product of DAICEL CHEMICAL INDUSTRIES, LTD.)
Eluant: 20 mM potassium phosphate buffer (pH 8.0)/acetonitrile=7/3
Flow rate: 0.5 ml/min
Column temperature: room temperature
Measurement wavelength: 210 nm

The invention claimed is:

1. An isolated DNA which encodes a polypeptide which is any one of the following polypeptides (b), and (c):
   (b) a polypeptide comprising an amino acid sequence derived from the amino acid sequence set forth in SEQ ID NO:1 by substitution, insertion, deletion, and/or addition of 90 or less amino acids, and having activity to selectively hydrolyze S-enantiomer in racemic nipecotamide and wherein the polypeptide is not SEQ ID NO: 1; and
   (c) a polypeptide having sequence identity of 80% or higher to the amino acid sequence set forth in SEQ ID NO:1, and having activity to selectively hydrolyze S-enantiomer in racemic nipecotamide and wherein the polypeptide is not SEQ ID NO: 1.

2. An isolated DNA which is any one of the following DNAs (a), (b), and (c):
   (b) a DNA hybridizable under a stringent condition with a DNA comprising a nucleotide sequence complementary to the nucleotide sequence set forth in SEQ ID NO:2, and encoding a polypeptide having activity to selectively hydrolyze S-enantiomer in racemic nipecotamide, and wherein the DNA does not comprise SEQ ID NO: 2, wherein the stringent condition is a condition where hybridization is carried out in the presence of 0.7 to 1.0 M NaCl, at 65° C., followed by washing the filter with 0.2-fold concentration of SSC solution at 65° C.; and (c) a DNA having sequence identity of 80% or higher to the nucleotide sequence set forth in SEQ ID NO:2, and encoding a polypeptide having activity to selectively hydrolyze S-enantiomer in racemic nipecotamide, and wherein the DNA does not comprise SEQ ID NO: 2.

3. The DNA according to claim 2, which has sequence identity of 85% or higher to the nucleotide sequence set forth in SEQ ID NO:2, and encodes the polypeptide having activity to selectively hydrolyze S-enantiomer in racemic nipecotamide.

4. A vector comprising an isolated DNA which encodes a polypeptide which is any one of the following polypeptides (a), (b), and (c):
   (a) a polypeptide comprising the amino acid sequence set forth in SEQ ID NO:1;
   (b) a polypeptide comprising an amino acid sequence derived from the amino acid sequence set forth in SEQ ID NO:1 by substitution, insertion, deletion, and/or addition of 90 or less amino acids, and having activity to selectively hydrolyze S-enantiomer in racemic nipecotamide; and
   (c) a polypeptide having sequence identity of 80% or higher to the amino acid sequence set forth in SEQ ID NO:1, and having activity to selectively hydrolyze S-enantiomer in racemic nipecotamide.

5. A transformant which is producible by transformation of a host microorganism with the vector according to claim 4, wherein said host microorganism is not *Cupriavidus* sp.

6. The transformant according to claim 5, wherein the host microorganism is *Escherichia coli*.

7. The isolated DNA according to claim 1 which encodes the polypeptide which has sequence identity of 85% or higher to the amino acid sequence set forth in SEQ ID NO:1, and has activity to selectively hydrolyze S-enantiomer in racemic nipecotamide.

8. The DNA according to claim 1, which is isolated from a microorganism belonging to the genus *Cupriavidus*.

9. The DNA according to claim 8, wherein the microorganism belonging to the genus *Cupriavidus* is *Cupriavidus* sp. KNK-J915 strain (FERM BP-10739).

10. A vector comprising an isolated DNA which is any one of the following DNAs (a), (b), and (c):
    (a) a DNA comprising the nucleotide sequence set forth in SEQ ID NO:2;
    (b) a DNA hybridizable under a stringent condition with a DNA comprising a nucleotide sequence complementary to the nucleotide sequence set forth in SEQ ID NO:2, and encoding a polypeptide having activity to selectively hydrolyze S-enantiomer in racemic nipecotamide, wherein the stringent condition is a condition where hybridization is carried out in the presence of 0.7 to 1.0 M NaCl, at 65° C., followed by washing the filter with 0.2-fold concentration of SSC solution at 65° C.; and (c) a DNA having sequence identity of 80% or higher to the nucleotide sequence set forth in SEQ ID No:2, and encoding a polypeptide having activity to selectively hydrolyze S-enantiomer in racemic nipecotamide.

* * * * *

SEQUENCE LISTING

<160> NUMBER OF SEQ ID NOS: 11

<210> SEQ ID NO 1
<211> LENGTH: 447
<212> TYPE: PRT

<213> ORGANISM: Cupriavidus sp.

<400> SEQUENCE: 1

```
Met Pro Thr Asp Ile Gln Thr Leu Gln Thr Arg Leu His Asp Gly Ala
1               5                   10                  15

Val Ser Arg Ala Asp Val Ile Ala Gln Ala Ala Gln His Ala Gln Gln
            20                  25                  30

Pro Asp Ala His Ala Val Phe Leu His Thr Thr Phe Asp Thr Ala Ala
        35                  40                  45

Gln Val Ala Lys Ala Ala Asp Ala Ala Cys Leu Ala Gly Lys Pro Leu
    50                  55                  60

His Pro Leu Ala Gly Leu Pro Val Ser Val Lys Asp Leu Phe Asn Ile
65                  70                  75                  80

Ala Gly Glu Ala Ser Arg Ala Gly Ser Pro Val Arg Ser Asp Ala Leu
                85                  90                  95

Ala Ala Thr Ala Asp Ala Thr Val Val Arg Leu Arg Glu Ser Gly
            100                 105                 110

Ala Ala Leu Val Gly Arg Thr Asn Met Thr Glu Phe Ala Phe Ser Gly
        115                 120                 125

Val Gly Ile Asn Pro His Phe Gly Thr Pro Val Asn Pro Ala Asp Lys
    130                 135                 140

Gln Val Ala Arg Ile Pro Gly Gly Ser Ser Gly Ala Ala Val Ser
145                 150                 155                 160

Val Ala Leu Gly Leu Ala Val Ala Gly Leu Gly Ser Asp Thr Gly Gly
                165                 170                 175

Ser Ile Arg Ile Pro Ala Ala Leu Cys Gly Leu Thr Gly Phe Lys Pro
            180                 185                 190

Thr Ala Arg Arg Val Pro Leu Asp Gly Ala Phe Pro Leu Ser Tyr Thr
        195                 200                 205

Leu Asp Thr Ala Cys Ala Met Ala Arg Thr Val Gln Asp Cys Val Leu
    210                 215                 220

Val Asp Ser Val Ile Ala Asp Gln Ala Val Leu Pro Val Ile Lys Gly
225                 230                 235                 240

Ala Ala Gly Ile Arg Leu Ala Ile Pro Arg Gln Val Leu Leu Asp Asp
                245                 250                 255

Leu Asp Asp Thr Val Ala Arg Ala Phe Asp Arg Ala Leu Gly Arg Leu
            260                 265                 270

Ser Ala Ala Gly Val Gln Ile Glu His Ile Asp Leu Pro Glu Leu Ala
        275                 280                 285

Glu Leu Ala Thr Ile Asn Ala Ser Gly Gly Phe Thr Ala Ala Glu Ala
    290                 295                 300

His Ala Ile His Arg His Val Leu Ala Thr Arg Arg Glu Gln Tyr Asp
305                 310                 315                 320

Pro Arg Val Ala Ser Arg Ile Asp Arg Gly Ala Ala Met Ser Ala Ala
                325                 330                 335

Asp Tyr Val Asp Leu Met Arg Ala Arg Leu Asp Trp Ile Thr Arg Val
            340                 345                 350

Ala Ala Arg Leu Glu Gly Phe Asp Ala Val Ala Cys Pro Thr Val Pro
        355                 360                 365

Met Val Ala Pro Pro Ile Ala Pro Leu Val Ala Asp Asp Ala Leu Phe
    370                 375                 380

Phe His Thr Asn Ala Leu Leu Leu Arg Asn Thr Ser Ala Phe Asn Phe
385                 390                 395                 400
```

```
Leu Asp Gly Cys Ser Ile Ser Leu Pro Cys His Gln Pro Asp Glu Leu
            405                 410                 415

Pro Val Gly Leu Met Leu Ser His Gly Ala Leu Arg Asp Ala Gln Leu
        420                 425                 430

Leu Gly Thr Ala Ile Ala Leu Glu Ser Ile Val Lys Pro Ala Ala
        435                 440                 445

<210> SEQ ID NO 2
<211> LENGTH: 1344
<212> TYPE: DNA
<213> ORGANISM: Cupriavidus sp.

<400> SEQUENCE: 2
atgcctacgg atatccagac attacagaca agacttcacg atggcgcggt ctcccgcgcc      60
gacgtgatcg cccaggctgc gcagcacgcg cagcagccgg acgcgcacgc cgtgttcctg     120
cacaccacct tcgacaccgc cgcgcaggtc gccaaggccg ccgacgcggc ctgcctggcg     180
ggcaagccgc tgcatccgct ggcaggcctg ccggtttcgg tcaaggacct gttcaacatc     240
gccggcgaag cctcgcgcgc cggctcgccg gtgcgcagcg acgcgctggc ggccacggcc     300
gacgccacgg tggtgcgccg gttgcgcgag agcggcgcgg cgctggtcgg cgcaccaac      360 atgaccgagt tcgccttctc gggcgtgggc atcaacccgc atttcggcac cccggtcaac     420
ccggcggaca gcaggtcgc gcgcattccc ggcggctcgt cgtcgggcgc cgcggtgtcc      480
gtggcgctgg gcctggcggt ggcggggctg ggcagcgaca ccggcggctc catccgcatc     540
ccggctgccc tgtgcgggct gaccggcttc aagccgaccg cccggcgcgt gccgctggac     600
ggcgccttcc cgctctccta tacgctggac accgcctgcg ccatggcgcg cacggtgcag     660
gattgcgtgc tggtggacag cgtgatcgcc gaccaggcgg tgctccccgt catcaagggc     720
gcagcgggca tccgcctggc catcccgcgc caggtcctgc ttgacgacct cgatgacacg     780
gtggcgcgcg cgttcgaccg cgccctcggc cggctgtccg cggccggcgt gcagatcgag     840
cacatcgacc tgccggagct ggccgagctg gccaccatca acgccagcgg cggcttcacc     900
gccgccgagg cgcatgccat ccaccgccac gtgctggcca cgcggcgcga gcaatacgat     960
ccgcgcgtag cgtcgcgcat cgaccgcggc gcggccatga gcgcggccga ctacgtggac    1020
ctgatgcgcg cccgcctcga ctggatcacg cgggttgccg cccgcctcga aggcttcgac    1080
gccgtggcct gccccaccgt gccgatggtg gcgccgccga tcgccccgct ggtggcggac    1140
gacgcgctgt tcttccacac caacgccctg ctgctgcgca atacgtcagc gttcaacttc    1200
ctcgatggct gctccatctc gctgccttgc caccagccgg acgagttgcc cgtgggcctg    1260
atgctctcgc acggtgcgct gcgcgacgcg caactgctgg gcacggcaat tgcattggaa    1320
tccatcgtca agccggccgc ctga                                           1344

<210> SEQ ID NO 3
<211> LENGTH: 20
<212> TYPE: DNA
<213> ORGANISM: Artificial
<220> FEATURE:
<223> OTHER INFORMATION: Primer 1
<220> FEATURE:
<221> NAME/KEY: misc_feature
<222> LOCATION: (12)..(12)
<223> OTHER INFORMATION: n represents a, t, g or c

<400> SEQUENCE: 3
gayathcara cnttrcarac                                                  20
```

```
<210> SEQ ID NO 4
<211> LENGTH: 20
<212> TYPE: DNA
<213> ORGANISM: Artificial
<220> FEATURE:
<223> OTHER INFORMATION: Primer 2
<220> FEATURE:
<221> NAME/KEY: misc_feature
<222> LOCATION: (3)..(3)
<223> OTHER INFORMATION: n represents a, t, g or c
<220> FEATURE:
<221> NAME/KEY: misc_feature
<222> LOCATION: (15)..(15)
<223> OTHER INFORMATION: n represents a, t, g or c

<400> SEQUENCE: 4
ccngcdatrt traanagrtc                                          20

<210> SEQ ID NO 5
<211> LENGTH: 24
<212> TYPE: DNA
<213> ORGANISM: Artificial
<220> FEATURE:
<223> OTHER INFORMATION: Primer 3

<400> SEQUENCE: 5
tggcaggcct gccggtttcg gtca                                     24

<210> SEQ ID NO 6
<211> LENGTH: 24
<212> TYPE: DNA
<213> ORGANISM: Artificial
<220> FEATURE:
<223> OTHER INFORMATION: Primer 4

<400> SEQUENCE: 6
ggagaccgcg ccatcgtgaa gtct                                     24

<210> SEQ ID NO 7
<211> LENGTH: 37
<212> TYPE: DNA
<213> ORGANISM: Artificial
<220> FEATURE:
<223> OTHER INFORMATION: Primer 5

<400> SEQUENCE: 7
agcatcgtac atatgcctac ggatatccag acattac                       37

<210> SEQ ID NO 8
<211> LENGTH: 38
<212> TYPE: DNA
<213> ORGANISM: Artificial
<220> FEATURE:
<223> OTHER INFORMATION: Primer 6

<400> SEQUENCE: 8
gcagaattct tatcaggcgg ccggcttgac gatggatt                      38

<210> SEQ ID NO 9
<211> LENGTH: 1356
<212> TYPE: DNA
<213> ORGANISM: Ralstonia eutropha JMP134

<400> SEQUENCE: 9
atgcttcctg acctcaacac actgcatgcc cgtctgcgcg aaggcgccat aagccgcgtc    60
gaactgatcg aagccgctgc cgatgcagcc tcccagccgc gcgcccaggc agtcttcctg   120
```

```
catagcacgt tcgataccgc cctccagacc gcccgcgccg ccgatgcggc gggccgtgcc    180
ggcaaagcgc tgcaccctct ggccggcttg ccggtttcgg tcaaggatct cttcgatgtg    240
gccggcgagg tcacgcgcgc agcctcggcg gtacggcacg acgctccccc ggcgacggcc    300
gacgccaccg tggtcgcacg cctgcgccac gccggtgcgg ccctggtcgg gcgcaccaac    360
atgaccgagt tcgccttctc gggcgtgggc atcaatcccc atttcggcac gccggtgaac    420
ccggcaagcg ccgatggtat cgcccgcatc cccggaggat cgtcgtcggg gcgggccgtt    480
tcggtggcac tcgggctggc ggtcgcggcg ctcggcagcg acacaggcgg atcgatccga    540
attcccgcag cgctgtgcgg cctgaccggg ttcaaaccga ccacgcgccg cgtgccgctg    600
accggcgcct ttccattgtc ctacacgctg acaccgcct gtgcgatggc tcgcacggtc     660
aatgactgcc tgctggtgga cagtgtaatt gccgacaacg cgctggtgcc aagcgctccc    720
gccgccgcgg cgcttcgcct ggccatcccg cgccaggtac tgctggacga cctcgacccc    780
gtggtcgcgc gcgcgttcga ccgcgcgctg gccgattgt cggccgccgg cgtgcagctg     840
gagcacaccg acctgcctga actcgccgaa ctcccgggcc tgaacgccgc aggcggcttc    900 agcgcggcc aggcctttc catccatcgc cacacactcg ccacgcggcg caacatgtac      960
gacccgcgcg ttgccctgcg cattgaccgc ggagcagcca tgggtgcagc ggactacgtc   1020
gatctggccc gcgcgcgcat cgactggatt tcacgcgtgg aagcccgcct cgcgcgcttt   1080
gatgcggtca tctgcccgac cgtgccgatg gtcgctcccg ccattgaacc gctgcgcgca   1140
gacgacgatt tgttcctccg caccaacgcg ctgctgcttc gcaataccto ggccttcaac   1200 ttcctcgacg gcggctcgat ctcgctgccc tgccatgcgc ccgacgaact gcccgtgggg   1260
ttgatgctgt cccatggccc catgcgcgat gcgcaattga tcggcaccgc ccttgcattg   1320
gaaagcatcg tgcagccttc cctgcgcgac gaataa                             1356

<210> SEQ ID NO 10
<211> LENGTH: 37
<212> TYPE: DNA
<213> ORGANISM: Artificial
<220> FEATURE:
<223> OTHER INFORMATION: Primer 7

<400> SEQUENCE: 10
agcatcgtac atatgcttcc tgacctcaac acactgc                              37

<210> SEQ ID NO 11
<211> LENGTH: 37
<212> TYPE: DNA
<213> ORGANISM: Artificial
<220> FEATURE:
<223> OTHER INFORMATION: Primer 8

<400> SEQUENCE: 11
gcagagctcc tattattcgt cgcgcaggga aggctgc                              37
```